United States Patent [19]

Ebata et al.

[11] Patent Number: 6,107,510
[45] Date of Patent: Aug. 22, 2000

[54] PROCESS FOR PRODUCING NITRILE COMPOUND AND CATALYST USED THEREFOR

[75] Inventors: Shuji Ebata; Hideaki Ogino; Takashi Okawa; Kinya Tsuji, all of Niigata-ken, Japan

[73] Assignee: Mitsubishi Gas Chemical Company, Inc., Tokyo, Japan

[21] Appl. No.: 09/225,553

[22] Filed: Jan. 5, 1999

[30] Foreign Application Priority Data

Jan. 16, 1998 [JP] Japan .................................. 10-006728
Mar. 4, 1998 [JP] Japan .................................. 10-052104

[51] Int. Cl.$^7$ .................................................. C07C 253/00
[52] U.S. Cl. ........................................... 558/327; 558/328
[58] Field of Search .................................... 558/327, 328; 546/286

[56] References Cited

U.S. PATENT DOCUMENTS 4,336,205  6/1982  Onishi et al. ........................... 260/465

Primary Examiner—Joseph McKane
Assistant Examiner—Joseph Murray
Attorney, Agent, or Firm—Antonelli, Terry, Stout & Kraus, LLP

[57] ABSTRACT

There are disclosed a process for producing a nitrile compound which comprises catalytically reacting an alkyl group-substituted aromatic compound or an alkyl group-substituted heterocyclic compound with a mixed gas containing ammonia and oxygen in the presence of ① a catalyst comprising a vanadium oxide, a chromium oxide, a boron oxide, a molybdenum oxide, and an oxide of an alkali metal or an alkaline earth metal or ② a catalyst comprising a vanadium oxide, a chromium oxide, a boron oxide, an alkali metal oxide, and a heteropolyacid. According to the above process and by virtue of the specific catalyst, it is made possible to produce a nitrile compound having an aromatic ring or a heterocyclic ring in an extremely advantageous manner, that is, in high yield at high selectivity to the objective product.

9 Claims, No Drawings

PROCESS FOR PRODUCING NITRILE COMPOUND AND CATALYST USED THEREFOR

BACKGROUND OF THE INVENTION

1. Field of the Invention

The present invention relates to a process for producing a nitrile compound and a catalyst to be used therefor. More particularly, the present invention is concerned with a process for producing a nitrile compound from a corresponding alkyl group-substituted aromatic compound or alkyl group-substituted heterocyclic compound and a mixed gas containing ammonia and oxygen; and with a catalyst to be used therefor.

2. Description of the Related Arts

A nitrile compound which is derived from an alkyl group-substituted aromatic compound is an important intermediate in organic chemical industries. Phthalonitrile as an example of said nitrile compound is used as a starting raw material for xylylenediamine which is useful as a curing agent for synthetic resins, agricultural chemicals, diisocyanate and epoxy resins. On the other hand, cyanopyridine which is derived from an alkyl group-substituted heterocyclic compound is used as a starting raw material for nicotinic acid amides and nicotinic acid that are useful substances in the industrial fields including pharmaceuticals, feed additives and food additives.

There have been proposed various processes for producing aromatic nitrites by subjecting an alkyl group-substituted aromatic compound to ammoxidation by the use of ammonia and oxygen. For example, Japanese Patent Publication No. 19284/1970 (Sho-45) describes a ternary catalyst consisting of vanadium, chromium and boron. Japanese Patent Publication No. 45860/1974 (Sho-49) describes a ternary catalyst which consists of vanadium, chromium and boron in the form of vanadium oxide, chromium oxide and boron oxide, respectively, in an atomic ratio of 1:(0.5 to 2.0):(0.1 to 1.2), and which is supported on silica as the carrier in an amount of 30 to 60% by weight based on said carrier. Japanese Patent Publication No. 15028/1976 (Sho-51) corresponding to U.S. Pat. No. 4,082,786 describes a quaternary catalyst which consists of a vanadium oxide, a chromium oxide, boron oxide and a phosphorus oxide in an atomic ratio of 1:(0.5 to 2.0):(0.1 to 1.2):(0.01 to 0.3). Further, Japanese Patent Application Laid-Open No. 275551/1989 (Hei-1) corresponding to U.S. Pat. No. 4,985,581 describes a quaternary catalyst consisting of a vanadium oxide, a chromium oxide, a molybdenum oxide and boron oxide in an atomic ratio of 1:(0.5 to 2.0):(0.01 to 1.2):(0.01 to 1.2).

On the other hand, as an example of process for producing a nitrile compound by subjecting a corresponding alkyl group-substituted heterocyclic compound to ammoxidation, Japanese Patent Application Laid-Open No. 275564/1989 (Hei-1) corresponding to U.S. Pat. No. 4,963,087 describes a process for producing cyanopyridine by reacting methylpyridine with ammonia and an oxygen-containing gas in the presence of a catalyst which consists of a vanadium oxide, a chromium oxide and boron oxide, and which is supported on silica as a carrier.

A large amount of reaction heat is generated in the case of ammoxidation reaction in which an alkyl group-substituted compound is reacted with ammonia and oxygen in a gas phase, thereby making it extremely difficult to properly control the reaction temperature. In order to overcome such an difficulty, a reactor of fluidized bed type is particularly effective. On the other hand, Japanese Patent Publication No. 15028/1976 (Sho-51) corresponding to U.S. Pat. No. 4,082,786 and Japanese Patent Application Laid-Open No. 275551/1989 (Hei-1) corresponding to U.S. Pat. No. 4,985,581 describe the improvement in the yield of a nitrile compound produced by ammoxidation by the use of a catalyst for a reactor of fluidized bed type. Likewise, Japanese Patent Publication No. 19284/1970 (Sho-45) and Japanese Patent Publication No. 45860/1974 (Sho-49) describe the improvement in the yield of a nitrile compound produced by ammoxidation through the addition of a phosphorus oxide and a molybdenum oxide to a vanadium oxide, a chromium oxide and boron oxide. Nevertheless, the yield of the nitrile compound is not necessarily sufficed by any of the above-mentioned prior arts.

SUMMARY OF THE INVENTION

A general object of the invention is to provide a process for producing a nitrile compound in high yield by the catalytic reaction between an alkyl group-substituted aromatic compound or an alkyl group-substituted heterocyclic compound, and a mixed gas containing ammonia and oxygen.

Under the above-mentioned circumstances, intensive research and investigation were accumulated by the present inventors in order to further enhance the yield of the nitrile compound to be produced by the ammoxidation reaction of an alkyl group-substituted aromatic compound or an alkyl group-substituted heterocyclic compound. As a result, it has been found that the yield of the nitrile compound produced by said ammoxidation reaction is remarkably enhanced by using a quinary catalyst which has a specific chemical composition and which comprises a quaternary catalyst comprising a vanadium oxide, a chromium oxide, a boron oxide and a molybdenum oxide that are supported on silica carrier, and further an alkali metal oxide or an alkaline earth metal oxide incorporated therein. The first aspect of the present invention has been accomplished by the foregoing findings and information.

That is to say, the first aspect of the present invention relates to a process for producing a nitrile compound which comprises catalytically reacting an alkyl group-substituted aromatic compound or an alkyl group-substituted heterocyclic compound with a mixed gas containing ammonia and oxygen in the presence of a catalyst comprising a vanadium oxide, a chromium oxide, a boron oxide, a molybdenum oxide, and an oxide of an alkali metal or an alkaline earth metal; and also relates to a catalyst for producing a nitrile compound which comprises a vanadium oxide, a chromium oxide, a boron oxide, a molybdenum oxide, and an oxide of an alkali metal or an alkaline earth metal that are supported on silica.

Moreover, further intensive research and investigation were accumulated by the present inventors in order that a high yield may be maintained in the production of the nitrile compound by said ammoxidation reaction. As a result, it has been found that the heat resistance of a catalyst is enhanced and at the same time, the yield of the nitrile compound produced by said ammoxidation reaction can be maintained for a long period of time by combinationally using a ternary catalyst which comprises a vanadium oxide, a chromium oxide and a boron oxide that are supported on silica, along with an alkali metal oxide and a heteropolyacid. The second aspect of the present invention has been accomplished by the aforesaid findings and information.

That is to say, the second aspect of the present invention relates to a process for producing a nitrile compound which comprises catalytically reacting an alkyl group-substituted aromatic compound or an alkyl group-substituted heterocyclic compound with a mixed gas containing ammonia and oxygen in the presence of a catalyst comprising a vanadium oxide, a chromium oxide, a boron oxide, an alkali metal oxide and a heteropolyacid; and also relates to a catalyst for producing a nitrile compound which comprises a vanadium oxide, a chromium oxide, a boron oxide, an alkali metal oxide and a heteropolyacid that are supported on silica.

DETAILED DESCRIPTION OF THE INVENTION

A variety of alkyl group-substituted aromatic compounds are available as a starting raw material in the present invention. Examples of preferable alkyl group-substituted aromatic compounds include an alkyl group-substituted benzene which possesses 1 to 4 alkyl groups each having 1 to 3 carbon atoms and which is exemplified by toluene, ethylbenzene and polymethylbenzene such as xylene, mesytylene, cymene and durene, and diethylbenzene; and an alkyl group-substituted naphthalene which possesses 1 to 4 alkyl groups each having 1 to 3 carbon atoms and which is exemplified by methylnaphthalene. A variety of alkyl group-substituted heterocyclic compounds are also available as a starting raw material in the present invention. Examples of preferable alkyl group-substituted heterocyclic compounds include an alkyl group-substituted pyridine which possesses 1 to 2 alkyl groups each having 1 to 3 carbon atoms and which is exemplified by methylpyridine, ethylpyridine and dimethylpyridine, and an alkyl group-substituted quinoline which possesses 1 to 2 alkyl groups each having 1 to 3 carbon atoms and which is exemplified by methylquinoline.

The suitable concentration of the foregoing alkyl group-substituted compound (alkyl group-substituted compound means alkyl group-substituted aromatic compound or alkyl group-substituted heterocyclic compound) in the gas to be fed to a reactor is 0.5 to 5 vol % in the case where air is used as an oxygen source.

The amount of ammonia to be used in the nitrile-forming reaction needs only to be at least the stoichiometric value, that is, one mole of ammonia per one mole of an alkyl group. The higher the molar ratio of the ammonia/an alkyl group-substituted compound is, the more advantageous the yield of the nitrile compound from the alkyl group-substituted compound is, but it is economically advantageous to set the molar ratio to at least the stoichiometric value, preferably to about 2 to 10 times said stoichiometric value.

Air is usually used as an oxygen source, and the oxygen source may be diluted with an inert diluent such as nitrogen, carbon dioxide and steam. The amount of oxygen to be supplied is at least 1.5 times, preferably 2 to 50 times its stoichiometric value.

The nitrile-forming reaction may be put into practice in a wide range of reaction temperatures from 300 to 500° C., preferably from 330 to 470° C. A reaction temperature, when being lower than 300° C., gives rise to a decrease in the conversion of the starting alkyl group-substituted compound, whereas a reaction temperature, when being higher than 500° C., brings about such evil effects as increase in the production of carbon dioxide and hydrogen cyanide, thus being accompanied by a decrease in the yield of objective nitile compound, and deteriorated catalyst resulting in shortened service time. Since the reaction temperature which exhibits a maximum yield of the nitile compound varies depending upon the type and concentration of the starting alkyl group-substituted compound, period of time of contact with the catalyst, the calcining temperature of the catalyst and the like conditions, it is preferable to properly select the reaction temperature in the above-mentioned range in accordance with these conditions. The period of time of contact between the reactant gas and the catalyst can generally be adopted in a considerably wide range, and is preferably in the range of 0.5 to 30 seconds.

The nitrile-forming reaction is carried out usually at atmospheric pressure, but may be performed under pressure or reduced pressure. The method for collecting the reaction product is selected from arbitrary appropriate methods including, for example, a method in which the reaction product is collected by being cooled to a temperature which is sufficient to precipitate the reaction product and a method in which the reaction product is collected by washing the reaction gas with water or a suitable organic solvent or the like. As mentioned hereinbefore, the nitrile-forming reaction in the present invention is accompanied by violent heat generation, and therefore, it is advantageous to carry out the reaction in a fluidized bed or a moving bed in the sense of removal of the reaction heat and the prevention of localized heating. Nevertheless, the reaction, even when carried out in a fixed bed, is capable of exhibiting its characteristics and also maintaining excellent performance.

The starting raw materials of the components of a vanadium oxide, a chromium oxide and boron oxide are stated hereunder. For a vanadium oxide, there are used ammonium metavanadate, vanadyl sulfate, a vanadium salt of an organic acid such as oxalic acid and tartaric acid, and the like. For a chromium oxide, there are used chromic acid, chromium nitrate, chromium hydroxide, ammonium chromate, ammonium dichromate, chromium salt of an organic acid such as oxalic acid and tartaric acid, and the like. For boron oxide, there are used boric acid and ammonium borate and the like.

In the catalyst of the first aspect of the present invention, a molybdenum oxide is used in addition thereto. For the starting raw material of a molybdenum oxide, there are used molybdic acid, ammonium paramolybdate, a molybdenum salt of an organic acid such as oxalic acid and tartaric acid, and the like.

The first aspect of the present invention is characterized in that an alkali metal or an alkaline earth metal is added as a catalyst component in addition to the foregoing four metallic oxide components.

As the starting raw materials for the alkali metal, there is suitably used any of a hydroxide, a carbonate, a nitrate, a salt of an organic acid such as oxalic acid, tartaric acid and acetic acid, each being derived from an alkali metal such as lithium, sodium, potassium, rubidium and cesium. As the starting raw materials for the alkaline earth metal, there is suitably used any of a hydroxide, a nitrate, a salt of an organic acid such as oxalic acid, tartaric acid and acetic acid, each being derived from an alkaline earth metal such as magnesium, calcium, strontium, and barium.

The atomic ratio of the catalyst components in the first aspect of the present invention, that is, vanadium:chromium:boron:molybdenum:alkali metal or alkaline earth metal is preferably in the range of 1:(0.5 to 2.0):(0.01 to 1.5):(0.01 to 1.5):(0.005 to 0.2). The atomic ratio thereof, when being outside the aforesaid range, leads to a decrease in the yield of the objective nitrile compound.

In the catalyst of the second aspect of the present invention, an alkali metal oxide and a heteropolyacid are used in addition to a vanadium oxide, a chromium oxide and boron oxide.

The alkali metal to be used in the catalyst of the second aspect of the present invention includes lithium, sodium, potassium, rubidium and cesium. As the starting raw materials for the alkali metal oxide component, there is suitably used any of a hydroxide, a carbonate, a nitrate, a salt of an organic acid such as oxalic acid, tartaric acid and acetic acid, each being derived from the above-mentioned alkali metal. Examples of the metallic components of the heteropolyacid are molybdenum, tungsten and vanadium. As the starting raw materials for the heteropolyacid, there are used phosphomolybdic acid, phosphotungstic acid, silico-tungstic acid, phosphovanadidotungstic acid and an ammonium salt thereof. In addition, as the starting raw materials for the alkali metal oxide and heteropolyacid, there are also usable an metal salt of a heteropolyacid such as sodium phosphomolybdate, sodium phosphotungstate, potassium silicotungstate and sodium silicotungstate.

Examples of preferable catalyst for the second aspect of the present invention are represented by the following general formula (I).

$$V_a Cr_b B_c X_d Y_{d/12} Z_e O_f \quad (I)$$

wherein V is vanadium which constitutes a vanadium oxide and excludes vanadium which constitutes a heteropolyacid; Cr is chromium which constitutes a chromium oxide; B is boron which constitutes boron oxide; X is at least one element which constitutes a heteropolyacid, and selected from the group consisting of Mo, W and V; Y is at least one element which constitutes a heteropolyacid, and selected from the group consisting of P, Si and Ge; and Z is at least one element which constitutes an alkali metal oxide, and selected from the group consisting of Li, Na, K, Rb and Cs. The atomic ratio of each of the elements, that is, a:b:c:d:e is preferably 1:(0.5 to 2.0):(0.01 to 1.5):(0.01 to 1.5):(0.005 to 0.2), and f is a value corresponding to the oxide which is formed by each of the elements being bonded to one another. The atomic ratio thereof, when being outside the aforesaid range, results in a decrease in the yield of the objective nitrile compound and a failure to assure the expected service life of the catalyst.

In both the first and second aspects of the present invention, there is preferably used the catalyst in which the above-described catalyst components are supported on silica. Examples of the silica used as said carrier include silica-gel, colloidal silica and anhydrous silica that are described in Chemistry Handbook, Applied Chemistry Section, pp 256 to 258, 1986, issued from Maruzen Co., Ltd. The content of the catalyst components is 20 to 80% by weight, preferably 30 to 60% by weight in terms of % by weight of the catalyst based on the total amount of the oxides calculated as the oxides including $V_2O_5$, $Cr_2O_3$, $B_2O_3$, $MoO_3$ and XeO, wherein X is at least one element selected from the group consisting of Li, Na, K, Rb, Cs, Mg, Ca, Sr and Ba; and e is an integer of 2 in the case of an alkali metal oxide, and 1 in the case of an alkaline earth metal oxide.

The catalyst according to the present invention can be produced by any of well known methods as described hereunder. For example, in the case of the catalyst for the first aspect of the present invention, a vanadium oxide and a chromium oxide are dissolved in oxalic acid, the resultant solution is incorporated with aqueous solution of boric acid, potassium acetate and molybdic acid, and then silica-sol is added to the mixture thus formed to obtain a mixed slurry. In the case of the catalyst for the second aspect of the present invention, a vanadium oxide and a chromium oxide are dissolved in oxalic acid, the resultant solution is incorporated with aqueous solution of ammonium paramolybdate, aqueous solution of boric acid, and potassium acetate or calcium acetate, and then silica-sol is added to the mixture thus formed to obtain a mixed slurry. In the aforestated procedure, there is used if needed, a dissolving assistant for boric acid, which is exemplified by a polyhydric alcohol, α-monoxycarboxylic acid and dioxycarboxylic acid. In the case of the catalyst for a fluidized bed, the resultant mixed slurry is spray-dried, further dried as necessary, at 110 to 150° C., and thereafter calcined. In the case of the catalyst for a fixed bed, the mixed slurry is evaporated to dryness, and thereafter calcined. The calcination is usually carried out at 400 to 700° C., preferably 450 to 650° C. for at least several hours under air ventilation. A preliminary calcination, when carried out at 200 to 400° C. prior to the calcination, leads to a more favorable result.

According to the first aspect of the present invention, the objective nitrile compound is obtained at an extremely high yield by subjecting the corresponding alkyl group-substituted aromatic compound or the corresponding alkyl group-substituted heterocyclic compound to ammoxidation through the use of the catalyst supported on a carrier which comprises a vanadium oxide, a chromium oxide, boron oxide, a molybdenum oxide, and an alkali metal oxide or an alkaline earth metal oxide.

Likewise, according to the second aspect of the present invention, the objective nitrile compound is obtained at a further high yield by carrying out the ammoxidation in the same manner as the foregoing through the use of the catalyst supported on a silica carrier which comprises a vanadium oxide, a chromium oxide, a boron oxide, an alkali metal oxide and a heteropolyacid with additional advantages in that said catalyst is enhanced in heat resistance and at the same time, is prolonged in its service life.

Such being the case, the present invention enables the nitrile compound having an aromatic ring or a heterocyclic ring to be produced in extremely industrially advantageous manners, thereby rendering itself highly significant from the industrial point of view.

In the following, the present invention will be described in more detail with reference to comparative examples and working examples, which however shall not limit the present invention thereto.

COMPARATIVE EXAMPLE 1

{Preparation of catalyst} To 229 g of vanadium pentoxide $V_2O_5$ was added 500 ml of water under heating to a temperature of 85° C., and to the resultant mixture was added 477 g of oxalic acid with sufficient stirring. Further 400 ml of water was added to 963 g of oxalic acid under heating to a temperature of 55° C., and to the resultant mixture was added a solution of 252 g of chromic acid anhydride $CrO_3$ in 200 ml of water with sufficient stirring to dissolve the reactants. The solution of vanadyl oxalate thus obtained was mixed with a solution of chromium oxalate at a temperature of 55° C. to obtain a solution of vanadium and chromium. On the other hand, to 44 g of ammonium para-molybdate $(NH_4)_6 Mo_7O_{24}.4H_2O$ was added 300 ml of water with sufficient stirring at a temperature of 40° C. To the previously obtained solution of vanadium and chromium was added the aqueous solution of the ammonium paramolybdate, and further 2501 g of 20% by weight of aqueous silica-sol. To the resultant slurry solution was added 78 g of boric acid $H_3BO_3$ with sufficient stirring, and the mixture thus formed was concentrated to reduce the liquid amount to 3800 g. The resultant catalyst solution was spray-dried with a spray drier, while maintaining the inlet and outlet temperatures at 250° C. and 130° C., respectively. The catalyst thus spray-dried was further dried with a drier at 130° C. for 12 hours, preliminarily calcined at 400° C. for 0.5 hour, and thereafter calcined at 550° C. for 8 hours in a stream of air. The objective catalyst had an atomic ratio V:Cr:B:Mo being 1:1:0.5:0.1, and contained 50% by weight of active ingredients.

{Activity test for catalyst} A reactor which had an inside diameter of 23 mm and which was heated with a resistance heating element was charged with 40 ml of the catalyst thus prepared, wherein a mixed gas consisting of 3.0 vol % of m-xylene, 21.0 vol % of ammonia and 76.0 vol % of air was subjected to fluid catalytic reaction under the conditions including a temperature of 370° C. at which this catalyst exerted a maximum yield of isophthalonitrile and an hourly space velocity SV of 750 $Hr^{-1}$.

As a result, there were obtained isophthalonitrile at a yield of 72.6 mole % based on m-xylene, and m-tolunitrile at a yield of 2.9 mole % based on the same at a selectivity to isophthalonitrile of 72.6 mole % based on the reacted m-xylene. Thereafter in order to predict the service life of the catalyst within a short period of time, a heat load was applied at 450° C. for 300 hours and then the catalyst was again subjected to fluid catalytic reaction at 370° C. As a result, the yield of the isophthalonitrile went down as low as 67.6 mole % at a selectivity to isohpthalonitrile of 68.1 mole %, while the yield of the m-tolunitrile was 2.6 mole %.

EXAMPLE 1

(First Aspect of the Invention)

{Preparation of catalyst} To 229 g of vanadium pentoxide $V_2O_5$ was added 500 ml of water under heating to a temperature of 85° C., and to the resultant mixture was added 477 g of oxalic acid with sufficient stirring. Further 400 ml of water was added to 963 g of oxalic acid under heating to a temperature of 55° C., and to the resultant mixture was added a solution of 252 g of chromic acid anhydride $CrO_3$ in 200 ml of water with sufficient stirring to dissolve the reactants. The solution of vanadyl oxalate thus obtained was mixed with a solution of chromium oxalate at a temperature of 55° C. to obtain a solution of vanadium and chromium. On the other hand, to 44 g of ammonium para-molybdate $(NH_4)_6 Mo_7O_{24}.4H_2O$ was added 300 ml of water with sufficient stirring at a temperature of 40° C. To the previously obtained solution of vanadium and chromium was added the aqueous solution of the ammonium paramolybdate. Subsequently 100 ml of water was added to 9.05 g of lithium carbonate $Li_2CO_3$ to dissolve the same and the resultant solution was added to the previously obtained mixed solution. Further 2501 g of 20% by weight of aqueous silica-sol was added to the mixed solution. To the resultant slurry solution was added 78 g of boric acid $H_3BO_3$ with sufficient stirring, and the mixture thus formed was concentrated to reduce the liquid amount to 3800 g. The resultant catalyst solution was spray-dried with a spray drier, while maintaining the inlet and outlet temperatures at 250° C. and 130° C., respectively. The catalyst thus spray-dried was further dried with a drier at 130° C. for 12 hours, preliminarily calcined at 400° C. for 0.5 hour, and thereafter calcined at 550° C. for 8 hours in a stream of air. The objective catalyst had an atomic ratio V:Cr:B:Mo:Li being 1:1:0.5:0.1:0.077, and contained 50% by weight of active ingredients.

{Activity test for catalyst} The catalyst prepared in the above-mentioned manner was subjected to activity test in the same manner as in Comparative Example 1. That is to say, a mixed gas consisting of 3.0 vol % of m-xylene, 21.0 vol % of ammonia and 76.0 vol % of air was subjected to fluid catalytic reaction under the conditions including a temperature of 390° C. at which this catalyst exerted a maximum yield of isophthalonitrile and an hourly space velocity SV of 750 $Hr^{-1}$.

As a result, there were obtained objective isophthalonitrile at a yield of 82.3 mole % based on m-xylene, and m-tolunitrile at a yield of 2.2 mole % based on the same at a selectivity to isophthalonitrile of 82.5 mole % based on the reacted m-xylene.

EXAMPLE 2

The procedure in Example 1 was repeated to prepare the catalyst and carry out an activity test for the catalyst except that sodium carbonate $Na_2CO_3$ was used in place of lithium carbonate. Thus the catalyst was prepared which had an atomic ratio V:Cr:B:Mo:Na being 1:1:0.5:0.2:0.046, and contained 50% by weight of active ingredients. Subsequently, a mixed gas consisting of 3.0 vol % of m-xylene, 21.0 vol % of ammonia and 76.0 vol % of air was subjected to fluid catalytic reaction under the conditions including a temperature of 410° C. at which this catalyst exerted a maximum yield of isophthalonitrile and an hourly space velocity SV of 750 $Hr^{-1}$.

As a result, there were obtained objective isophthalonitrile at a yield of 81.7 mole % based on m-xylene, and m-tolunitrile at a yield of 2.8 mole % based on the same at a selectivity to isophthalonitrile of 81.9 mole % based on the reacted m-xylene.

EXAMPLE 3

The procedure in Example 1 was repeated to prepare the catalyst and carry out an activity test for the catalyst except that potassium acetate $CH_3COOK$ was used in place of lithium carbonate. Thus the catalyst was prepared which had an atomic ratio V:Cr:B:Mo:K being 1:1:0.5:0.2:0.027, and contained 50% by weight of active ingredients. Subsequently, a mixed gas consisting of 3.0 vol % of m-xylene, 21.0 vol % of ammonia and 76.0 vol % of air was subjected to fluid catalytic reaction under the conditions including a temperature of 410° C. at which this catalyst exerted a maximum yield of isophthalonitrile and an hourly space velocity SV of 750 $Hr^{-1}$.

As a result, there were obtained objective isophthalonitrile at a yield of 86.4 mole % based on m-xylene, and m-tolunitrile at a yield of 2.6 mole % based on the same at a selectivity to isophthalonitrile of 86.7 mole % based on the reacted m-xylene.

EXAMPLE 4

The procedure in Example 1 was repeated to prepare the catalyst and carry out an activity test for the catalyst except that calcium acetate $(CH_3COO)_2 Ca$ was used in place of lithium carbonate. Thus the catalyst was prepared which had an atomic ratio V:Cr:B:No:Ca being 1:1:0.5:0.2:0.039, and contained 50% by weight of active ingredients. Subsequently, a mixed gas consisting of 3.0 vol % of m-xylene, 21.0 vol % of ammonia and 76.0 vol % of air was subjected to fluid catalytic reaction under the conditions including a temperature of 410° C. at which this catalyst exerted a maximum yield of isophthalonitrile and an hourly space velocity SV of 750 $Hr^{-1}$.

As a result, there were obtained objective isophthalonitrile at a yield of 85.1 mole % based on m-xylene, and m-tolunitrile at a yield of 1.9 mole % based on the same at a selectivity to isophthalonitrile of 85.5 mole % based on the reacted m-xylene.

EXAMPLE 5

The procedure in Example 1 was repeated to prepare the catalyst and carry out an activity test for the catalyst except that p-xylene was used in place of m-xylene by the use of the catalyst as prepared in Example 3 in place of Example 1. Thus, a mixed gas consisting of 3.2 vol % of p-xylene, 19.5 vol % of ammonia and 77.3 vol % of air was subjected to fluid catalytic reaction under the conditions including a temperature of 400° C. at which this catalyst exerted a maximum yield of terephthalonitrile and an hourly space velocity SV of 800 $Hr^{-1}$.

As a result, there were obtained objective terephthalonitrile at a yield of 85.9 mole % based on p-xylene, and p-tolunitrile at a yield of 1.5 mole % based on the same at a selectivity to terephthalonitrile of 86.1 mole % based on the reacted p-xylene.

EXAMPLE 6

The procedure in Example 1 was repeated to prepare the catalyst and carry out an activity test for the catalyst except that toluene was used in place of m-xylene by the use of the catalyst as prepared in Example 3 in place of Example 1. Thus, a mixed gas consisting of 5.1 vol % of toluene, 25.5 vol % of ammonia and 69.9 vol % of air was subjected to fluid catalytic reaction under the conditions including a temperature of 410° C. at which this catalyst exerted a maximum yield of benzonitrile and an hourly space velocity SV of 840 $Hr^{-1}$.

As a result, there were obtained objective benzonitrile at a yield of 83.5 mole % based on toluene at a selectivity to benzonitrile of 83.9 mole % based on the reacted toluene.

EXAMPLE 7

The procedure in Example 1 was repeated to prepare the catalyst and carry out an activity test for the catalyst except that 3-methylpyridine was used in place of m-xylene. Specifically, a mixed gas consisting of 3.0 vol % of 3-methylpyridine, 12.0 vol % of ammonia and 85.0 vol % of air was subjected to fluid catalytic reaction under the conditions including a temperature of 390° C. at which this catalyst exerted a maximum yield of 3-cyanopyridine and an hourly space velocity SV of 750 $Hr^{-1}$.

As a result, there were obtained objective cyanopyridine at a yield of 93.3 mole % based on 3-methylpyridine at a selectivity to 3-cyanopyridine of 93.6 mole % based on the reacted 3-methylpyridine.

EXAMPLE 8
(Second Aspect of the Invention)

{Preparation of catalyst} To 229 g of vanadium pentoxide $V_2O_5$ was added 500 ml of water under heating to a temperature of 85° C., and to the resultant mixture was added 477 g of oxalic acid with sufficient stirring. Further 400 ml of water was added to 963 g of oxalic acid under heating to a temperature of 55° C., and to the resultant mixture was added a solution of 252 g of chromic acid anhydride $CrO_3$ in 200 ml of water with sufficient stirring to dissolve the reactants. The solution of vanadyl oxalate thus obtained was mixed with a solution of chromium oxalate at a temperature of 55° C. to obtain a solution of vanadium and chromium. The resultant solution was mixed with a solution of 89.6 g of phosphomolybdic acid $H_3[PMo_{12}O_{40}].30H_2O$ in 100 ml of water, and to the resultant mixture was added a solution of 8.3 g of potassium acetate $CH_3COOK$ in 100 ml of water. Further, 2501 g of 20% by weight of aqueous silica-sol was added to the mixed solution. To the resultant slurry solution was added 78 g of boric acid $H_3BO_3$ with sufficient stirring, and the mixture thus formed was concentrated to reduce the liquid amount to 3800 g. The resultant catalyst solution was spray-dried with a spray drier, while maintaining the inlet and outlet temperatures at 250° C. and 130° C., respectively. The catalyst thus spray-dried was further dried with a drier at 130° C. for 12 hours, preliminarily calcined at 400° C. for 0.5 hour, and thereafter calcined at 550° C. for 8 hours in a stream of air. The catalyst thus obtained had an atomic ratio V:Cr:B:W:P:K being 1:1:0.5:0.1:0.008:0.027, and contained 50% by weight of active ingredients.

{Activity test for catalyst} The catalyst prepared in the above-mentioned manner was subjected to activity test in the same manner as in Comparative Example 1. That is to say, a mixed gas consisting of 3.0 vol % of m-xylene, 21.0 vol % of ammonia and 76.0 vol % of air was subjected to fluid catalytic reaction under the conditions including a temperature of 390° C. at which this catalyst exerted a maximum yield of isophthalonitrile and an hourly space velocity SV of 750 $Hr^{-1}$.

As a result, there were obtained objective isophthalonitrile at a yield of 89.1 mole % based on m-xylene, and m-tolunitrile at a yield of 2.6 mole % based on the same at a selectivity to isophthalonitrile of 89.3 mole % based on the reacted m-xylene. Subsequently, a heat load was applied at 450° C. for 300 hours and then the catalyst was again subjected to fluid catalytic reaction at 390° C. As a result, the yield of isophthalonitrile was 88.0 mole % based on m-xylene, and the yield of m-tolunitrile was 2.5 mole % based on he same at a selectivity to isophthalonitrile of 88.4 mole % based on the reacted m-xylene.

EXAMPLE 9

A catalyst was prepared in the same manner as in Example 8 except that the sodium carbonate $Na_2CO_3$ and silicotungstic acid were used in place of potassium acetate and molybdic acid, respectively. The resultant catalyst which had an atomic ratio V:Cr:B:W:Si:Na being 1:1:0.5:0.1:0.008:0.046 was subjected to an activity test in the same manner as in Example 1. Specifically, a mixed gas consisting of 3.0 vol % of m-xylene, 21.0 vol % of ammonia and 76.0 vol % of air was subjected to fluid catalytic reaction under the conditions including a temperature of 410° C. at which this catalyst exerted a maximum yield of isophthalonitrile and an hourly space velocity SV of 750 $Hr^{-1}$.

As a result, there were obtained objective isophthalonitrile at a yield of 88.9 mole % based on m-xylene, and m-tolunitrile at a yield of 2.5 mole % based on the same at a selectivity to isophthalonitrile of 89.0 mole % based on the reacted m-xylene. Subsequently, a heat load was applied at 450° C. for 300 hours and then the catalyst was again subjected to fluid catalytic reaction at 390° C. As a result, the yield of isophthalonitrile was 88.1 mole % based on m-xylene, and the yield of m-tolunitrile was 2.6 mole % based on the same at a selectivity to isophthalonitrile of 88.3 mole % based on the reacted m-xylene.

EXAMPLE 10

The procedure in Example 1 was repeated to prepare the catalyst and carry out an activity test for the catalyst except that p-xylene was used in place of m-xylene by the use of the catalyst as prepared in Example 8. Specifically, a mixed gas consisting of 3.2 vol % of p-xylene, 19.5 vol % of ammonia and 77.3 vol % of air was subjected to fluid catalytic reaction under the conditions including a temperature of 400° C. at which this catalyst exerted a maximum yield of terephthalonitrile and an hourly space velocity SV of 800 $Hr^{-1}$.

As a result, there were obtained objective terephthalonitrile at a yield of 89.5 mole % based on p-xylene, and p-tolunitrile at a yield of 1.3 mole % based on the same at a selectivity to terephthalonitrile of 89.7 mole % based on the reacted p-xylene. Subsequently, a heat load was applied at 450° C. for 300 hours and then the catalyst was again subjected to fluid catalytic reaction at 390° C. As a result, the yield of terephthalonitrile was 89.1 mole % based on p-xylene, and the yield of p-tolunitrile was 1.1 mole % based on the same at a selectivity to terephthalonitrile of 89.2 mole % based on the reacted p-xylene.

EXAMPLE 11

The procedure in Example 8 was repeated to prepare the catalyst and carry out an activity test for the catalyst except that 3-methylpyridine was used in place of m-xylene. Specifically, a mixed gas consisting of 3.0 vol % of 3-methylpyridine, 21.0 vol % of ammonia and 76.0 vol % of air was subjected to fluid catalytic reaction under the conditions including a temperature of 390° C. at which this catalyst exerted a maximum yield of 3-cyanopyridine and an hourly space velocity SV of 750 $Hr^{-1}$.

As a result, there were obtained objective cyanopyridine at a yield of 91.8 mole % based on 3-methylpyridine at a selectivity to 3-cyanopyridine of 92.2 mole % based on the reacted 3-methylpyridine. Subsequently, a heat load was applied at 450° C. for 300 hours and then the catalyst was again subjected to fluid catalytic reaction at 390° C. As a result, the yield of 3-cyanopyridine was 91.0 mole % based on 3-methylpyridine at a selectivity to 3-cyanopyridine of 92.8 mole % based on the reacted 3-methylpyridine.

What is claimed is:

1. A process for producing a nitrile compound which comprises catalytically reacting an alkyl group-substituted aromatic compound or an alkyl group-substituted heterocyclic compound with a mixed gas containing ammonia and oxygen in the presence of a catalyst comprising a vanadium oxide, a chromium oxide, a boron oxide, a molybdenum oxide, and an oxide of an alkali metal or an alkaline earth metal.

2. The process for producing a nitrile compound according to claim 1, wherein the catalyst consists essentially of a vanadium oxide, a chromium oxide, a boron oxide, a molybdenum oxide, and an oxide of an alkali metal or an alkaline earth metal.

3. The process for producing a nitrile compound according to claim 1, wherein the alkali metal or an alkaline earth metal is at least one element selected from the group consisting of lithium, sodium, potassium, rubidium, cesium, magnesium, calcium, strontium and barium.

4. The process for producing a nitrile compound according to claim 1, wherein the catalyst has an atomic ratio of vanadium:chromium:boron:molybdenum:an alkali metal or an alkaline earth metal being 1:(0.5 to 2.0):(0.01 to 1.5): (0.01 to 1.5):(0.005 to 0.2).

5. The process for producing a nitrile compound according to claim 1, wherein the catalyst comprising a vanadium oxide, a chromium oxide, a boron oxide, a molybdenum oxide, and an oxide of an alkali metal or an alkaline earth metal, is supported on silica in an amount of 20 to 80% by weight based on said silica.

6. A process for producing a nitrile compound which comprises catalytically reacting an alkyl group-substituted aromatic compound or an alkyl group-substituted heterocyclic compound with a mixed gas containing ammonia and oxygen in the presence of a catalyst comprising a vanadium oxide, a chromium oxide, a boron oxide, an alkali metal oxide, and a heteropolyacid.

7. The process for producing a nitrile compound according to claim 6, wherein the catalyst consists essentially of a vanadium oxide, a chromium oxide, a boron oxide, an alkali metal oxide, and a heteropolyacid.

8. The process for producing a nitrile compound according to claim 6, wherein the catalyst comprising a vanadium oxide, a chromium oxide, a boron oxide, an alkali metal oxide, and a heteropolyacid is an oxide represented by the general formula (1)

$$V_a Cr_b B_c X_d Y_{d/12} Z_e O_f \tag{1}$$

wherein V is vanadium which constitutes a vanadium oxide; Cr is chromium which constitutes a chromium oxide; B is boron which constitutes a boron oxide; X is at least one element which constitutes a heteropolyacid, and selected from the group consisting of Mo, W, and V; Y is at least one element which constitutes a heteropolyacid, and selected from the group consisting of P, Si and Ge; Z is at least one element which constitutes an alkali metal oxide, and selected from the group consisting of Li, Na, K, Rb and Cs; the atomic ratio among the elements, namely a:b:c:d:e is 1:(0.5 to 2.0):(0.01 to 1.5):(0.01 to 1.5):(0.005 to 0.2); and f is a value corresponding to the oxide which is formed by each of said elements being bonded to one another.

9. The process for producing a nitrile compound according to claim 6, wherein the catalyst comprising a vanadium oxide, a chromium oxide, a boron oxide, an alkali metal oxide, and a heteropolyacid, is supported on silica in an amount of 20 to 80% by weight based on said silica.

* * * * *